(12) United States Patent
Balter et al.

(10) Patent No.: US 12,207,911 B2
(45) Date of Patent: Jan. 28, 2025

(54) HIERARCHICAL MOTION MODELING FROM DYNAMIC MAGNETIC RESONANCE IMAGING

(71) Applicant: THE REGENTS OF THE UNIVERSITY OF MICHIGAN, Ann Arbor, MI (US)

(72) Inventors: James Balter, Ann Arbor, MI (US); Yue Cao, Ann Arbor, MI (US); Lianli Liu, Ann Arbor, MI (US); Adam Johansson, Uppsala (SE)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 844 days.

(21) Appl. No.: 17/364,845

(22) Filed: Jun. 30, 2021

(65) Prior Publication Data

US 2022/0007969 A1      Jan. 13, 2022

Related U.S. Application Data

(60) Provisional application No. 63/049,777, filed on Jul. 9, 2020.

(51) Int. Cl.
| | | |
|---|---|---|
| *A61B 5/055* | (2006.01) | |
| *G01R 33/565* | (2006.01) | |
| *G06T 7/207* | (2017.01) | |
| *G01R 33/48* | (2006.01) | |

(52) U.S. Cl.
CPC ........ *A61B 5/055* (2013.01); *G01R 33/56509* (2013.01); *G06T 7/207* (2017.01); *G01R 33/4826* (2013.01); *G06T 2207/10088* (2013.01)

(58) Field of Classification Search
CPC ....... A61B 5/113; A61B 5/721; A61B 5/0044; A61B 6/486; A61B 6/5264; G01R 33/56509; G01R 33/246; G01R 33/5673; G01R 33/5676
See application file for complete search history.

(56) References Cited

U.S. PATENT DOCUMENTS

| | | | | |
|---|---|---|---|---|
| 2010/0290683 A1* | 11/2010 | Demeester | ............... | A61B 5/33 |
| | | | | 382/131 |
| 2015/0309147 A1* | 10/2015 | Schmitter | ............ | G01R 33/443 |
| | | | | 600/410 |
| 2019/0113587 A1* | 4/2019 | Paulson | ............. | G01R 33/4808 |

OTHER PUBLICATIONS

Acharya et al., Online Magnetic Resonance Image Guided Adaptive Radiation Therapy: First Clinical Applications, Int. J. Radiat. Oncol. Biol. Phys., 94(2):394-403, (2016).
Alyami et al., Magnetic resonance imaging to evaluate gastrointestinal function, Neurogastroenterol. Motil., 27(12):1687-92, (2015).

(Continued)

*Primary Examiner* — Gerald Johnson
(74) *Attorney, Agent, or Firm* — MARSHALL, GERSTEIN & BORUN LLP

(57) ABSTRACT

The following relates generally to motion prediction in magnetic resonance (MR) imaging. In some embodiments, a "modular" approach is taken to motion correction. That is, individual motion sources (e.g., a patient's breathing, heartbeat, stomach contractions, peristalsis, and so forth) are accounted for individually in the motion correction. In some embodiments, to correct for a particular motion source, a reference state is created from a volume of interest (VOI), and other states are created and deformably aligned to the reference state.

19 Claims, 11 Drawing Sheets

(56) References Cited

OTHER PUBLICATIONS

Balter et al., Daily targeting of intrahepatic tumors for radiotherapy, Int. J. Radiat. Oncol. Biol. Phys., 52(1):266-71, (2002).
Birchfield et al., Statistical Considerations in the Creation of Realistic Synthetic Power Grids for Geomagnetic Disturbance Studies, *IEEE Transactions on Power Systems*, 32(2), 1502-1510, (2017).
Birchfield et al., Grid Structural Characteristics as Validation Criteria for Synthetic Networks, *IEEE Transactions on Power Systems*, 32(4): 3258-3265, (2017).
Bohoudi et al., Fast and robust online adaptive planning in stereotactic MR-guided adaptive radiation therapy (SMART) for pancreatic cancer, Radiother. Oncol., 125(3):439-44, (2017).
Campbell, *CRS Report for Congress Weather-Related Power Outages and Electric System Resiliency Specialist in Energy Policy Weather-Related Power Outages and Electric System Resiliency Congressional Research Service Weather-Related Power Outages and Electric System Resiliency Congressional Research Service*, (2012).
Cao et al., Prediction of liver function by using magnetic resonance-based portal venous perfusion imaging, Int. J. Radiat. Oncol. Biol. Phys., 85(1):258-63, (2013).
Davidson et al., Electric Power Distribution System Performance in Carolina Hurricanes, *Natural Hazards Review*, 4(1): 36-45, (2003).
De Jonge et al., Evaluation of gastrointestinal motility with MRI: Advances, challenges and opportunities, Neurogastroenterol. Motil., 30(1):1-7, (2018).
Eisenbach Consulting LLC, 9 of the Worst Power Outages in United States History, Retrieved from Electric Choice website: https://www.electricchoice.com/blog/worst-power-outages-in-united-states-history/, (2017).
Fischer-Valuck et al., Two-and-a-half-year clinical experience with the world's first magnetic resonance image guided radiation therapy system, Adv. Radiat. Oncol., 2(3):485-93, (2017).
Guikema et al., Hybrid data mining-regression for infrastructure risk assessment based on zero-inflated data, *Reliability Engineering and System Safety*, 99: 178-182, (2012).
Guikema et al., Statistical models of the effects of tree trimming on power system outages, *IEEE Transactions on Power Delivery*, 21(3): 1549-1557, (2006).
Guikema et al., Prestorm Estimation of Hurricane Damage to Electric Power Distribution Systems, *Risk Analysis*, 30(12): 1744-1752, (2010).
Guikema et al., Predicting Hurricane Power Outages to Support Storm Response Planning, *IEEE Access*, 2: 1364-1373, (2014).
Han et al., Improving the predictive accuracy of hurricane power outage forecasts using generalized additive models, *Risk Analysis*, 29(10): 1443-1453, (2009).
Henke et al., Phase I trial of stereotactic MR-guided online adaptive radiation therapy (SMART) for the treatment of oligometastatic or unresectable primary malignancies of the abdomen, Radiother Oncol., 126(3):519-26, (2018).
Henke et al., Simulated Online Adaptive Magnetic Resonance-Guided Stereotactic Body Radiation Therapy for the Treatment of Oligometastatic Disease of the Abdomen and Central Thorax: Characterization of Potential Advantages, Int. J. Radiat. Oncol. Biol. Phys., 96(5):1078-86, (2016).
Hoad et al., Colon wall motility: Comparison of novel quantitative semi-automatic measurements using cine MRI, Neurogastroenterol. Motil., 28(3):327-35, (2016).
Jiang et al., Outcomes Utilizing MRI-Guided and Real-Time Adaptive Pancreas Stereotactic Body Radiotherapy (SBRT), Int. J. Radiat. Oncol., 99(2):S146, (2017).
Johansson et al., Rigid-body motion correction of the liver in image reconstruction for golden-angle stack-of-stars DCE MRI, Magn. Reson. Med., 79(3):1345-53, (2018).
Johansson et al., Abdominal DCE-MRI reconstruction with deformable motion correction for liver perfusion quantification, Med. Phys., (2018).

Kezunovic et al., Predicting Spatiotemporal Impacts of Weather on Power Systems Using Big Data Science, Data Science and Big Data: An Environment of Computational Intelligence, 265-299, (2017).
Kircher et al., HAZUS Earthquake Loss Estimation Methods, *Natural Hazards Review*, 7(2): 45-59, (2006).
Lammers et al., Similarities and differences in the propagation of slow waves and peristaltic waves, Am. J. Physiol. Liver. Physiol., 283(3):G778-86, (2002).
Lischalk et al., Four-dimensional computed tomography prediction of inter- and intrafractional upper gastrointestinal tumor motion during fractionated stereotactic body radiation therapy, Pract. Radiat. Oncol., 6(3):176-82, (2016).
Liu et al., Statistical forecasting of electric power restoration times in hurricanes and ice storms, *IEEE Transactions on Power Systems*, 22(4): 2270-2279 (2007).
Marciani et al., Antral motility measurements by magnetic resonance imaging, Neurogastroenterol. Motil., 13(5):511-8, (2001).
Menys et al., Dual registration of abdominal motion for motility assessment in free-breathing data sets acquired using dynamic MRI, Phys. Med. Biol., 59(16):4603-19, (2014).
Miranda et al., Genetic algorithms in optimal multistage distribution network planning, *IEEE Transactions on Power Systems*, 9(4): 1927-1933 (1994).
Mittauer et al., TU-AB-BRA-11: Indications for Online Adaptive Radiotherapy Based On Dosimetric Consequences of Interfractional Pancreas-To-Duodenum Motion in MRI-Guided Pancreatic Radiotherapy, Med. Phys., 43(6Part33):1, (2018).
Darestani et al., Multi-dimensional wind fragility functions for wood utility poles, *Engineering Structures*, 183: 937-948, (2019).
Nateghi et al., Power Outage Estimation for Tropical Cyclones: Improved Accuracy with Simpler Models, *Risk Analysis*, 34(6): 1069-1078, (2014).
O'Grady et al., Origin and propagation of human gastric slow-wave activity defined by high-resolution mapping, AJP Gastrointest. Liver Physiol., 299(3):G585-92, (2010).
Pahwa et al., Abruptness of cascade failures in power grids, Scientific Reports, 4:3694, (2014).
Han et al., Estimating the spatial distribution of power outages during hurricanes in the gulf coast region, *Reliability Engineering and System Safety*, 94: 199-210, (2008).
Rudra et al., High Dose Adaptive MRI Guided Radiation Therapy Improves Overall Survival of Inoperable Pancreatic Cancer, Int. J. Radiat. Oncol., 99(2):E184, (2017).
Salman et al ., Age-dependent fragility and life-cycle cost analysis of wood and steel power distribution poles subjected to hurricanes, *Structure and Infrastructure Engineering*, 12(8): 890-903, (2016).
Schultz et al., A random growth model for power grids and other spatially embedded infrastructure networks, *The European Physical Journal Special Topics*, 223(12): 2593-2610, (2014).
Shafieezadeh et al., Age-dependent fragility models of utility wood poles in power distribution networks against extreme wind hazards, *IEEE Transactions on Power Delivery*, 29(1): 131-139, (2014).
Shashaani et al., Multi-Stage Prediction for Zero-Inflated Hurricane Induced Power Outages, *IEEE Access*, 6: 62432-62449, (2018).
Simeth et al., Quantification of liver function by linearization of a 2-compartment model of gadoxetic-acid uptake using dynamic contrast enhanced magnetic resonance imaging, NMR Biomed., 31(6):e3913 1-15, (2018).
Soltan et al., Generation of synthetic spatially embedded power grid networks, *IEEE Power and Energy Society General Meeting*, (2016).
Valenzuela et al., Planning of a Resilient Underground Distribution Network Using Georeferenced Data, *Energies*, 12(4): 644, (2019).
Vanzi, Seismic reliability of electric power networks: Methodology and application, *Structural Safety*, 18(4): 311-327, (1996).
Vickery et al., HAZUS-MH Hurricane Model Methodology. II: Damage and Loss Estimation, *Natural Hazards Review*, 7(2): 94-103, (2006).
Johansson et al., Gastrointestinal 4D MRI with respiratory motion correction, Med. Phys., 48(5): 2521-2527, (Feb. 2021).

\* cited by examiner

Radial sampling of k-space

HIERARCHICAL MOTION MODELING FROM DYNAMIC MAGNETIC RESONANCE IMAGING

CROSS-REFERENCE TO RELATED APPLICATIONS

This application claims the benefit of U.S. Provisional Application No. 63/049,777 (filed Jul. 9, 2020), the entirety of which is incorporated by reference herein.

STATEMENT OF GOVERNMENT INTEREST

This invention was made with government support under EB016079 awarded by the National Institutes of Health. The government has certain rights in the invention.

BACKGROUND

In typical Magnetic Resonance Imaging (MRI), physiologic or voluntary motions tend to corrupt images. This is especially true for abdominal imaging, where several different motions such as breathing, antral contraction, heartbeat, peristalsis and other motions interactively combine.

The systems and methods disclosed herein provide solutions to this problem and others.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one aspect, there is a computer-implemented method for real time display of a magnetic resonance (MR) image using a multitemporal technique, the method may include, via one or more processors, receiving k-space data acquired from an MR signal. The method may further include using the k-space data to: (i) build a motion model, wherein the motion model includes a first temporal resolution; and (ii) build a prediction model, wherein the prediction model includes a first prediction latency time. The method may still further include: correcting both the motion model and the prediction model to account for a first type of patient motion; and displaying the MR image based on both the corrected motion model and the corrected prediction model.

In another aspect, there is a computer-implemented method for real time display of an MR image, the method may include, via one or more processors: receiving k-space data acquired from an MR signal; and determining an MR image from the k-space data. The method may further include correcting the MR image to account for a first type of motion, wherein the first type of motion comprises a breathing motion, and wherein the correcting the MR image for the first type of motion occurs by: (i) determining a plurality of spokes in the k-space data; (ii) labeling at least one spoke of the plurality of spokes with a breathing amplitude of a patient; (iii) placing the at least one spoke into a bin of a plurality of bins, wherein each bin of the plurality of bins corresponds to a breathing state of a plurality of breathing states, and wherein one breathing state of the plurality of breathing states is an exhale state; (iv) selecting the exhale state as a reference state; and (v) deformably aligning the other breathing states to the reference state. The method may still further include correcting, to account for a second type of motion, the MR image that was corrected for the first type of motion.

In yet another aspect, there is a computer-implemented method for real time display of an MR image, the method may include, via one or more processors: receiving k-space data acquired from an MR signal; determining an MR image from the k-space data; and correcting the MR image to account for a first type of motion. The method may further include correcting, to account for a second type of motion, the MR image that was corrected for the first type of motion by: defining, in the MR image corrected for the first type of motion, a volume of interest (VOI) comprising a plurality of voxels; creating a reference phase for the VOI; determining, from the MR image corrected for the first type of motion, a set of image volumes demonstrating the second type of motion; and deformably aligning the set of image volumes to the reference phase.

The systems and methods disclosed herein advantageously improve upon existing techniques for motion correction in MR imaging. Further advantages will be recognized by the following disclosure.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

DETAILED DESCRIPTION

Overview

Often in MRI, physiologic or voluntary motions corrupt images. This is especially true for abdominal imaging, where several different motions such as breathing, antral contraction, heartbeat, peristalsis and other motions interactively combine. While various scanning techniques as well as reconstruction methods have been developed to partially assess and/or compensate for some of these motions, no known solution to date has been able to isolate, measure and account for the individual motion components.

The systems and methods described herein propose such a solution to this problem, and have imminent applications for precision radiation therapy (e.g., in guiding patient model development for safe treatment planning as well as targeting/tracking strategies for treatment delivery). The proposed solutions described herein may also have broader applications in guiding diagnostic assessments of intestinal motion, various gastrointestinal disorders, as well as aiding biomechanical modeling and assessments for a wide range of applications including modeling of impacts trauma (e.g., from car crashes). The proposed solutions described herein further have imminent applications for support of free-breathing dynamic contrast enhanced (DCE) MRI for both tissue enhancement as well as pharmacokinetic modeling.

As mentioned, the disclosed techniques account for patient motion. More specifically, the disclosed techniques separate motion sources (e.g., a patient's breathing, heartbeat, stomach contractions, peristalsis, and so forth), thus taking a "modular" approach to motion compensation in MRI.

Figure 1:
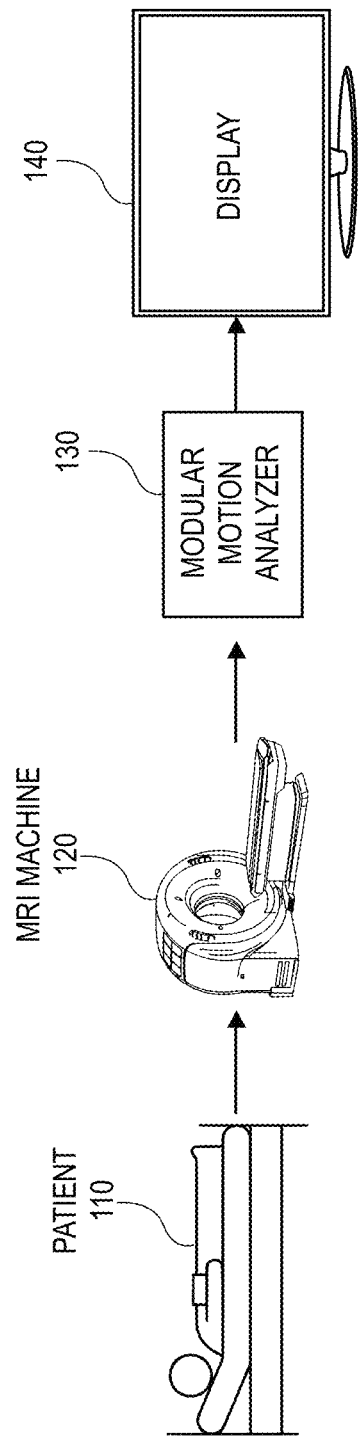
FIG. 1 illustrates an example embodiment including a modular motion analyzer.

By way of brief overview and illustrative example, FIG. 1 shows patient 110 entering an MRI machine 120. The MRI machine 120 may produce k-space data that is analyzed and processed by the modular motion analyzer 130. The display 140 is then controlled (e.g., by the modular motion analyzer 130) to display real time images of the patient 110).

As is understood in the art, the k-space data may comprise a grid of raw data, in a form such as $(k_x, k_y)$, acquired directly from the MR signal. Further, the k-space data may comprise an array of numbers representing spatial frequencies (e.g., a number of wave cycles per unit distance) in the MR image. As is further understood in the art, the k-space data may be converted to MR image using a Fourier Transform. Each point in k-space includes spatial frequency and phase information about every point (e.g., pixel) in the final MR image; thus, each point in k-space maps to every point in the final MR image.

Figure 2:
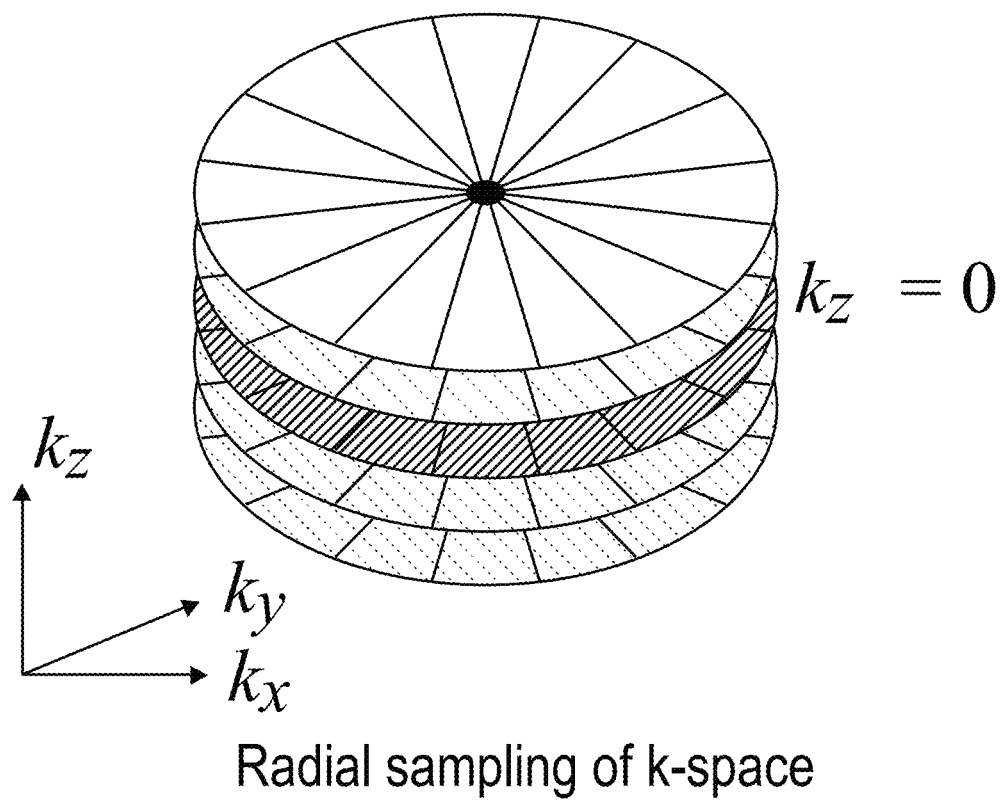
FIG. 2 shows an example radial sampling of k-space, including a stack of stars configuration.

Further regarding the k-space data, FIG. 2 shows an example of radial sampling of k-space. As can be seen, the sampling of individual lines (herein referred to as "spokes"), collect information for partitions (e.g., "slices") of the patient. This configuration is herein referred to as "stack of stars."

Example Embodiments

A method is herein disclosed that uses dynamic MR signals to measure and separate different motion sources. Although many of the disclosed techniques are described with reference to motion sources in the abdomen, the disclosed techniques are applicable to other portions of the body as well (e.g., the pelvis, lungs, neck, or any other part of the body). The described method is based on the premise that motions from sources such as breathing, heartbeat, stomach contraction, peristalsis and other physiological effects that modify abdominal configuration are primarily not temporally synchronized, and thus can be separated. In one implementation, three forms of temporally separate motion, as well as injected contrast dynamics, are extracted. Using a golden angle radial stack of stars acquisition, a series of stacks of k-space lines are acquired over a period of time (see, e.g., the example of FIG. 2).

To further explain the golden angle aspect, as is understood in geometry, the golden angle is the smaller of two angels formed by dividing a circumference of a circle according to the golden ratio ($\varphi$). It should be understood that two quantities are in golden ratio if the ratio of the two quantities is the same as the ratio of their sum to the larger of the two quantities.

The golden angle between spokes is intended to maximally separate successive samples in order to span as much of k-space as possible in any given number of samples. Any individual spoke can be considered to be the temporal center of the patient configuration at the time it was acquired, but its reconstruction generates only a projection, and not the complete structure, of the patient's abdomen at that time point. Including temporally neighboring spokes increases the information, and thus spatial resolution of the patient representation, but decreases the temporal resolution and thus is subject to spatial blurring of the reconstruction due to physiological motion.

Such MRI data acquisition can occur with or without the use of a contrast agent, as the contrast dynamics are also primarily orthogonal to motion dynamic signals. Regarding this optional contrast agent, it should be understood that the use of a contrast agent may improve visibility of an internal body structure within the MR image. This is because the contrast agent may, for example, shorten a relaxation time of nuclei within body tissues. The contrast agent may be administered by injection or orally.

Example Technique for Accounting for a Breathing Motion

The motion modeling disclosed takes advantage of knowledge of the nature of various motions and contrast dynamics. In this regard, breathing is typically the most dominant contributor to geometric configuration changes in the abdomen on short time scales.

Figure 3:
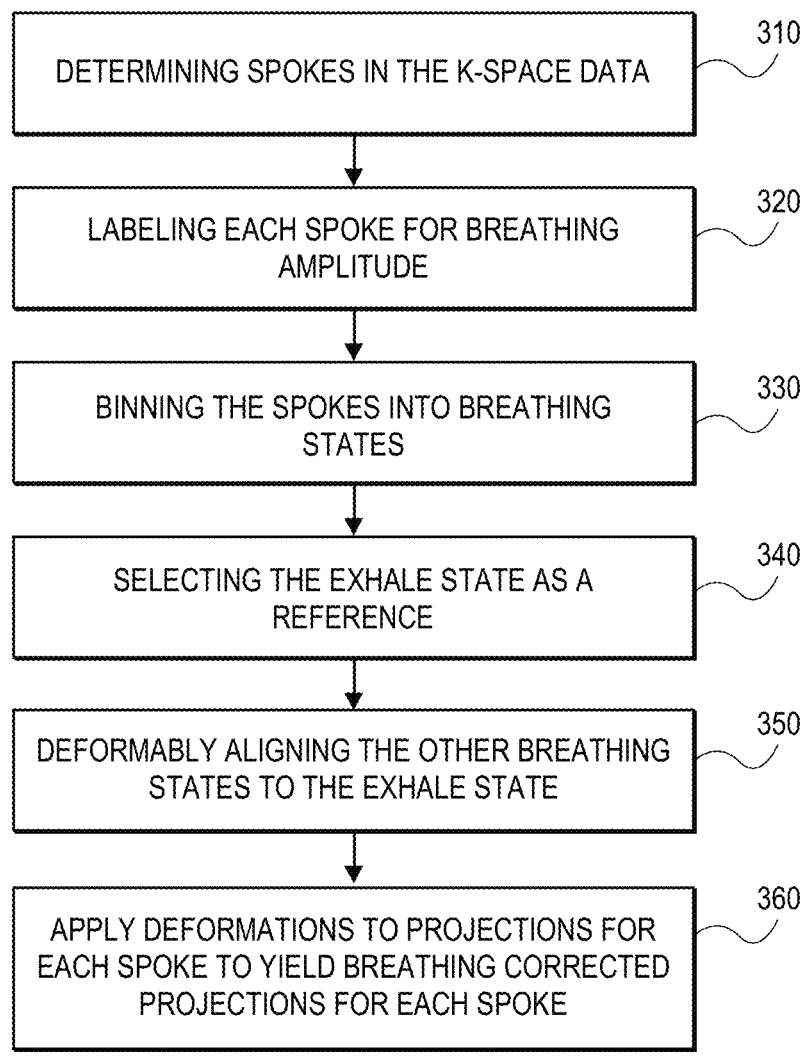
FIG. 3 shows an example flowchart for accounting for a breathing motion.

FIG. 3 shows an example flowchart for accounting for a breathing motion. At an initial step 310, spokes are determined in the k-space data. Then, at step 320, spokes are labeled for breathing amplitude. In some embodiments, this is done by performing a high temporal but low spatial resolution reconstruction centered on each spoke, generating an image volume wherein the liver (e.g., the organ that typically moves the most during breathing) or other organ is sufficiently resolved. These image volumes are rigidly aligned to optimally match the liver to its location in a reference (exhale in this example) state, and the cranial-caudal motion associated with the alignment transformation is used to label the amplitude of breathing for the patient at the time the spoke was acquired. As should be understood, rigid alignment and deformable alignment are both transforms applied to locations. However, as a practical matter, deformable alignment has potentially a vastly increased number of variables (degrees of freedom) to resolve, and as such is both slower as well as prone to uncertainties in results.

Figure 4:
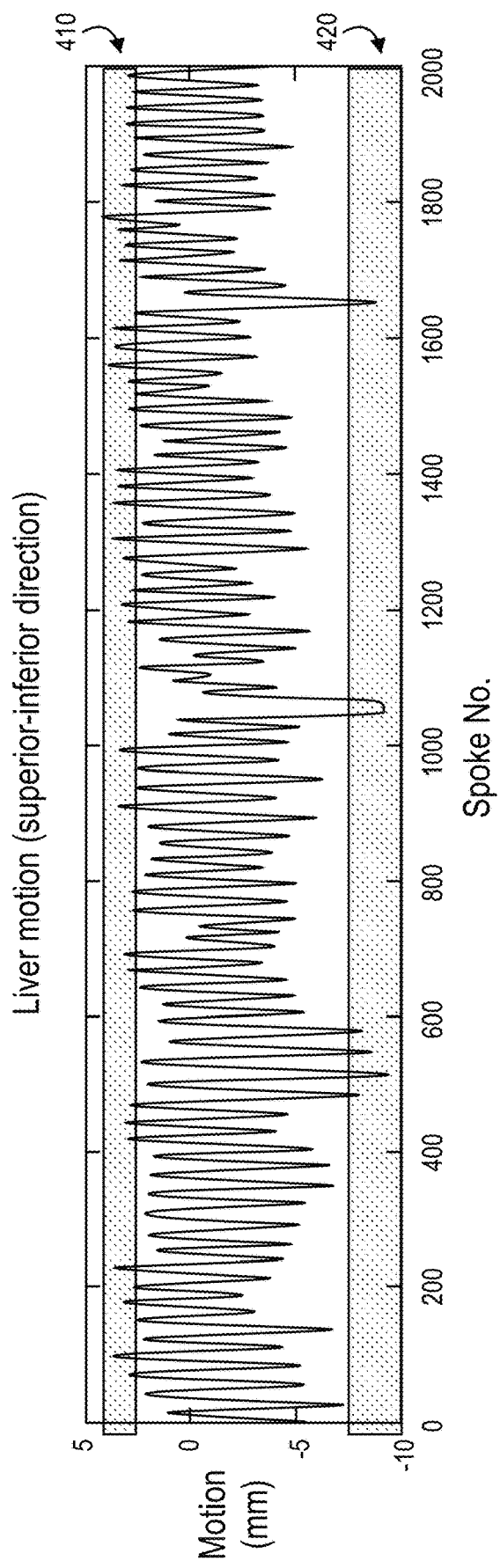
FIG. 4 shows an example of binning based on liver motion.

After all spokes are labeled for breathing amplitude, binning into separate breathing states is performed at step 330. To illustrate binning, FIG. 4 shows an example of binning based on liver motion. With reference thereto, the x-axis shows the spoke number, and the y-axis show the liver motion in mm. In some embodiments, bins are created based on a position of an organ (e.g., in the example of FIG. 4, a liver). In other embodiments, the bins are created based on the position of a reference point. In this regard, the example of FIG. 4 illustrates the bins as shaded areas 410, 420. As illustrated, the spokes in the shaded areas 410, 420 are placed in the corresponding bin. Although the example of FIG. 4 illustrates two bins, any number of bins may be used. For instance, in one example implementation, 21 binned states are created, with all spokes with breathing amplitudes assigned to a given bin collected and used for a separate conventional reconstruction, thus yielding high resolution image volumes indicative of each of the 21 breathing states.

Returning to FIG. 3, at step 340, the exhale state is chosen as a reference. At step 350, the other 20 image volumes are deformably aligned to the exhale representation, yielding deformation vector fields for each binned state. Explained another way, a deformation vector field, comprised of a plurality of vectors demonstrating displacements distributed at locations in the space occupied by the imaged volume, is created for a binned state by deformably aligning the image volume representing the binned state to the image volume representing the reference state (e.g., the exhale state). At step 360, these deformations (e.g., the deformation vectors) are then applied to the projections for each spoke according to their binned amplitudes, yielding breathing-corrected projections at each spoke. Performing reconstructions on such corrected data essentially removes breathing motion from resulting image volumes, allowing for several uses including dynamic contrast analysis and improved image reconstruction quality in the liver, as well as subsequent visualization and extraction of other motion states.

Figure 5:
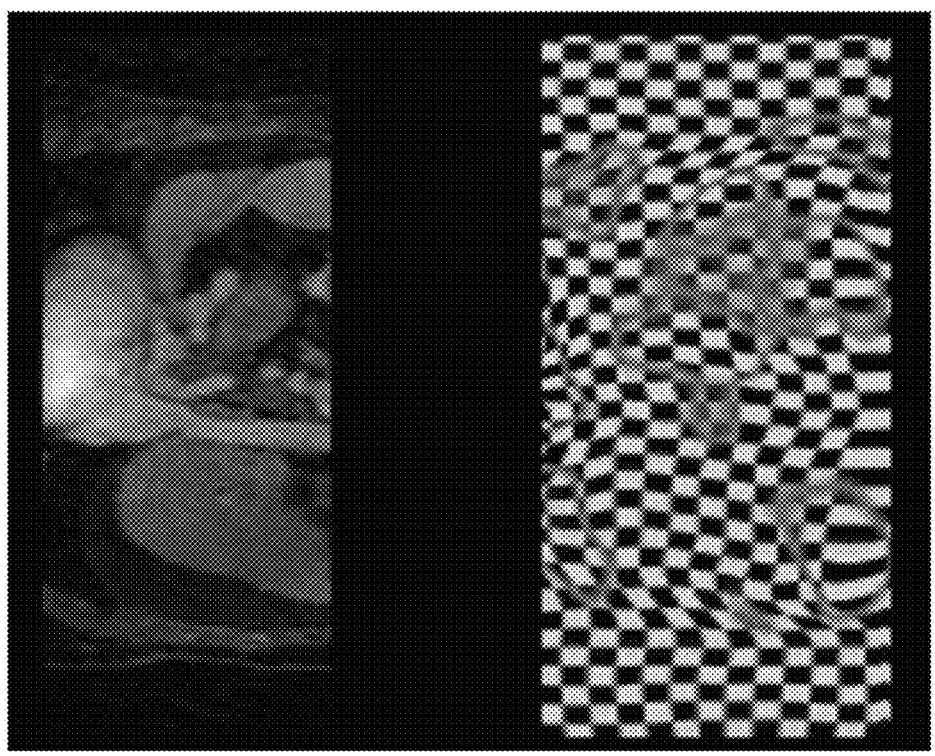
FIG. 5A illustrates an MR image in a reference state.
FIG. 5B illustrates an MR image corresponding to the MR image of FIG. 5A, but in a deformed state.
Figure 5:
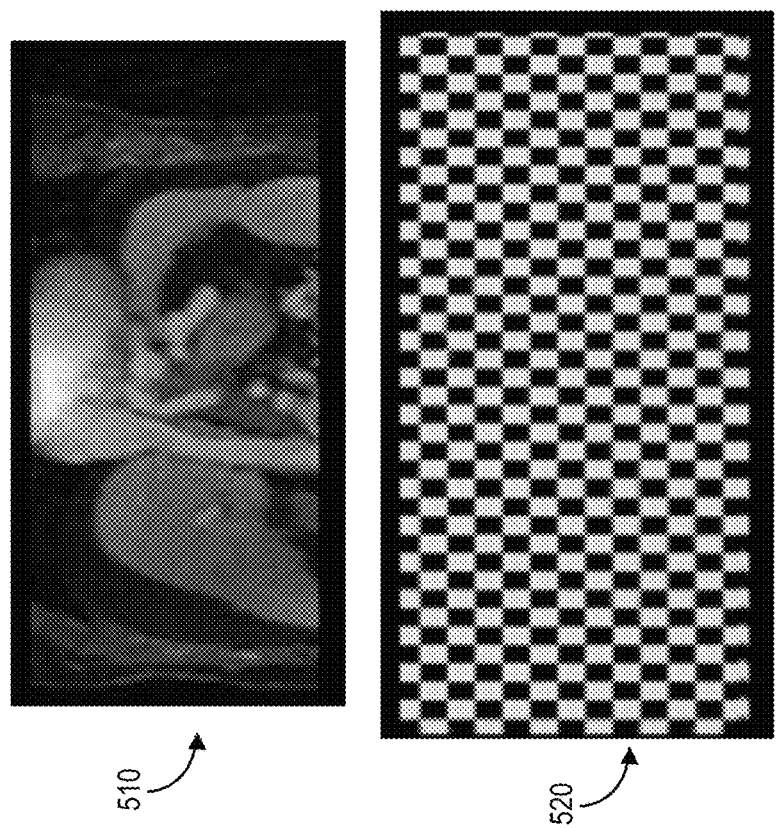

To illustrate the deformation aspects, FIG. 5A illustrates a coronal plane through a MR image in the reference state 520. That is, FIG. 5A illustrates an image of a rectangular grid matching the locations of voxels in the MR image slice 510 with the reference state. FIG. 5B illustrates an MR image 530 corresponding to the location of the coronal slice through the MR image volume shown in MR image 510 of FIG. 5A, but reconstructed from a different binned breathing state. State 540 represents the deformation of 510, via a deformation vector field that was measured through alignment of the reference and binned state and then applied to the voxel locations in MR image 510.

Example Technique for Accounting for a Gastric Motion

Figure 6:
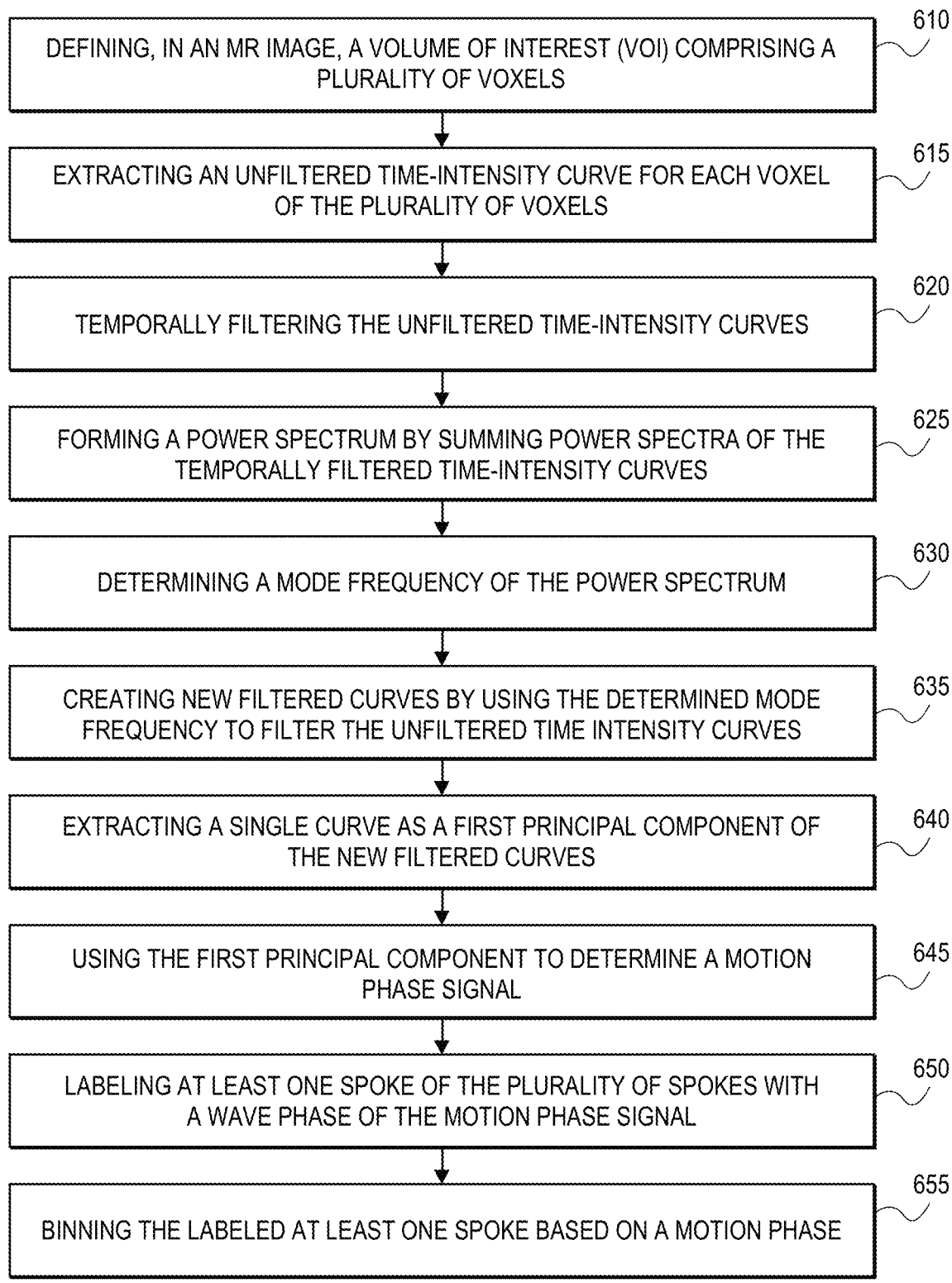
FIG. 6 shows an example flowchart for accounting for a second type of motion, such as a gastric motion.

FIG. 6 shows an example flowchart for accounting for a second type of motion, such as a gastric motion. In some embodiments, the process of FIG. 6 is performed after correcting for a first type of motion, such as by performing the steps of FIG. 3 to correct for a breathing motion. In other embodiments, the steps of FIG. 6 may be performed in a standalone fashion, without first correcting for a first type of motion.

Antral contractions of the stomach (e.g., gastric motions) generally tend to be more cyclically reproducible than breathing motions, and more importantly occur with a temporal frequency that is much lower than that of breathing (e.g., the breathing motion periodicity is shorter than the gastric motion periodicity). In this regard, some embodiments may correct the MR image for any number of types of motions by correcting the MR image for each type of motion sequentially in the order of motion with shortest periodicity to motion with longest periodicity. For example, the breathing motion has a shorter periodicity than the gastric motion so these embodiments correct for the breathing motion prior to correcting for the gastric motion.

In some implementations, the cyclic states of antral contraction (e.g., gastric motion) are extracted from analysis of intensity within a volume of interest (VOI) (defined, e.g., at step 610 of FIG. 6) encompassing the stomach on breathing motion-corrected image volume reconstructions generated using a view-sharing filter with a temporal resolution that varies from 2 seconds at the center to 58 seconds at the periphery of k-space, although these times can be altered as needed. For each voxel in the VOI, a time-intensity curve is extracted from the motion corrected image time-series at step 615. The resulting time-intensity curves are temporally filtered (e.g., at step 620) using a spectral Rician filter with a modulation transfer function given by the probability density function of the Rice distribution with non-centrality parameter v=3/min and scale parameter σ=1/min to emphasize gastric motion patterns which typically have a frequency of approximately 3/min. A total power spectrum is then formed at step 625 by summing the power spectra of the individual curves. A mode frequency is then determined from the power spectrum at step 630.

To further explain, the Rician filter is a spectral filter with a modulation transfer function given by the probability density function of the Rice distribution. Where the Rice distribution is:

$$\frac{x}{\sigma^2} \exp\left(\frac{-(x^2 + v^2)}{2\sigma^2}\right) I_0\left(\frac{xv}{\sigma^2}\right)$$

Where x is a frequency in spectrum; v is a non-centrality parameter; and σ is a scale parameter.

At step 635, the determined mode frequency in the power spectrum is then used as the non-centrality parameter for a new Rician temporal filter with scale parameter 0.25/min that is applied to the original time-intensity curves. A single curve is extracted as the first principal component of all the filtered curves at step 640. At step 645, the gastric motion phase signal is then determined as phi=a tan 2(y, x) where x is the first principal component and y its derivative. Because gastric motion can be described as a contraction wave travelling along the stomach, phi describes the position of this wave. Each spoke is thus labeled according to its gastric wave phase (e.g., at step 650), and again binning of spokes at matched antral contraction phases is performed (e.g., at step 655), and breathing motion-corrected projections at matching antral contraction phases are reconstructed, yielding image volumes that demonstrate stomach contraction uncorrupted by breathing motion. If desired, these volumes can be deformably aligned to a reference phase (e.g., as in the example of FIGS. 5A and 5B), producing a set of deformations versus contraction state as a dynamic model of stomach contraction and its influence on the motion of the stomach and surrounding abdominal anatomy.

Additional Motions

In addition to the roughly cyclic motions from breathing and antral contraction, the slower configuration changes of the abdomen are further measureable using the described methodology. These motions combine to yield a much slower temporal change in the relative configuration of the abdomen, and stomach cyclic motion can to first order be considered to be an orthogonal blurring function over the time periods considered in the current instance (although they could also be corrected if deemed necessary for specific applications). In some embodiments, using the breathing motion-corrected projections, full image volume reconstructions are created every n seconds using a m second time window. In one example, n=17 and m=34. These high resolution image volumes show the changes of abdominal configuration uncorrupted by the otherwise dominant breathing motion. In addition to demonstrating motion dynamics, deformable alignment of these slow motion states yields information for modeling and tracking abdominal anatomy over time scales consistent with typical radiation therapy treatments.

Exemplary Uses

The reconstructed image volumes for each of the three mentioned example motion states have immediate utility for a number of exemplary uses. These include, but are not limited to:
  i. Perfusion and/or liver function estimation from free-breathing dynamic contrast enhanced acquisitions;
  ii. Selection of optimal temporal reconstructions for enhanced visualization of tumor and normal liver contrast following injection of a contrast agent;
  iii. Aiding delineation of abdominal organs to assist Radiation Oncology treatment planning and/or patient positioning; and
  iv. Visualizing various abdominal physiological motions for diagnostic purposes.

The motion patterns due to breathing, antral contraction and slow configuration changes can be used for several purposes including, but not limited to:
  i. Statistical analysis of frequency and magnitude of motion states (e.g., for aiding estimated delivered radiation dose under various assumptions of management of breathing and/or other motions);
  ii. Guiding expansion of tumor and/or normal organ volumes to describe their locations (either complete motion over sampled time or constructs based on frequencies of space occupied and possible extrapolations);
  iii. Simulation and selection of various motion management as well as positioning and targeting techniques including, for example, breath hold, gating various ranges of breathing motion, and/or monitoring specific normal tissue anatomy position;
  iv. Quantitative assessment of physiological motions (e.g., for diagnostic and/or gastroenterology purposes); and
  v. Dynamic biomechanical modeling of abdominal motility.

Hierarchical models can be built from these motion states. The estimated actual patient configuration at any given time can be assembled by deforming the reference state (e.g., the exhale configuration of the patient at the reference cyclic stomach motion state and at the beginning time point of the scanning cycle) with the measured breathing, antral contraction and slow configuration states interpolated to the location of any given point in time. In addition, the dynamics of motions (or their subsets) can be simulated to show the effects of breathing or other motion management interventions on subsequent patient configuration. To support such hierarchical motion modeling, each sample location can be assigned a multidimensional description of state. In some embodiments, two variations of such hierarchical models are implemented. In the first model, three dimensions of motion states are labeled as breathing amplitude, antral contraction phase, and time. The first two dimensions (breathing amplitude and antral contraction phase) allow for interpolation of the relative deformations extracted due to breathing and stomach contraction. The third dimension (time) allows for interpolation of deformations from the temporally neighboring slow motion reconstructions. In a second model, statistical decompositions (e.g., Principal Components) of deformations are extracted, and/components can be assigned to each motion state. This latter implementation allows for the potential to reduce any possible impacts of uncertainty in deformation modeling, and further can be used to simplify the deformations to a small number of dominant modes. Such an implementation has a direct advantage of efficiency for near real-time applications such as motion monitoring during radiation therapy treatment or abdominal interventional treatments with or without MR guidance, as described below.

Multiple Temporal Resolution Monitoring of Abdominal Motions

A motion prediction method can be constructed based on the hierarchical motion model. In this regard, the disclosed methods are capable of real time estimation for breathing motion and slow configuration changes, with sub-millimeter accuracy, and with example uses in maintaining precision of MR-guided radiation or other therapies.

Figure 7:
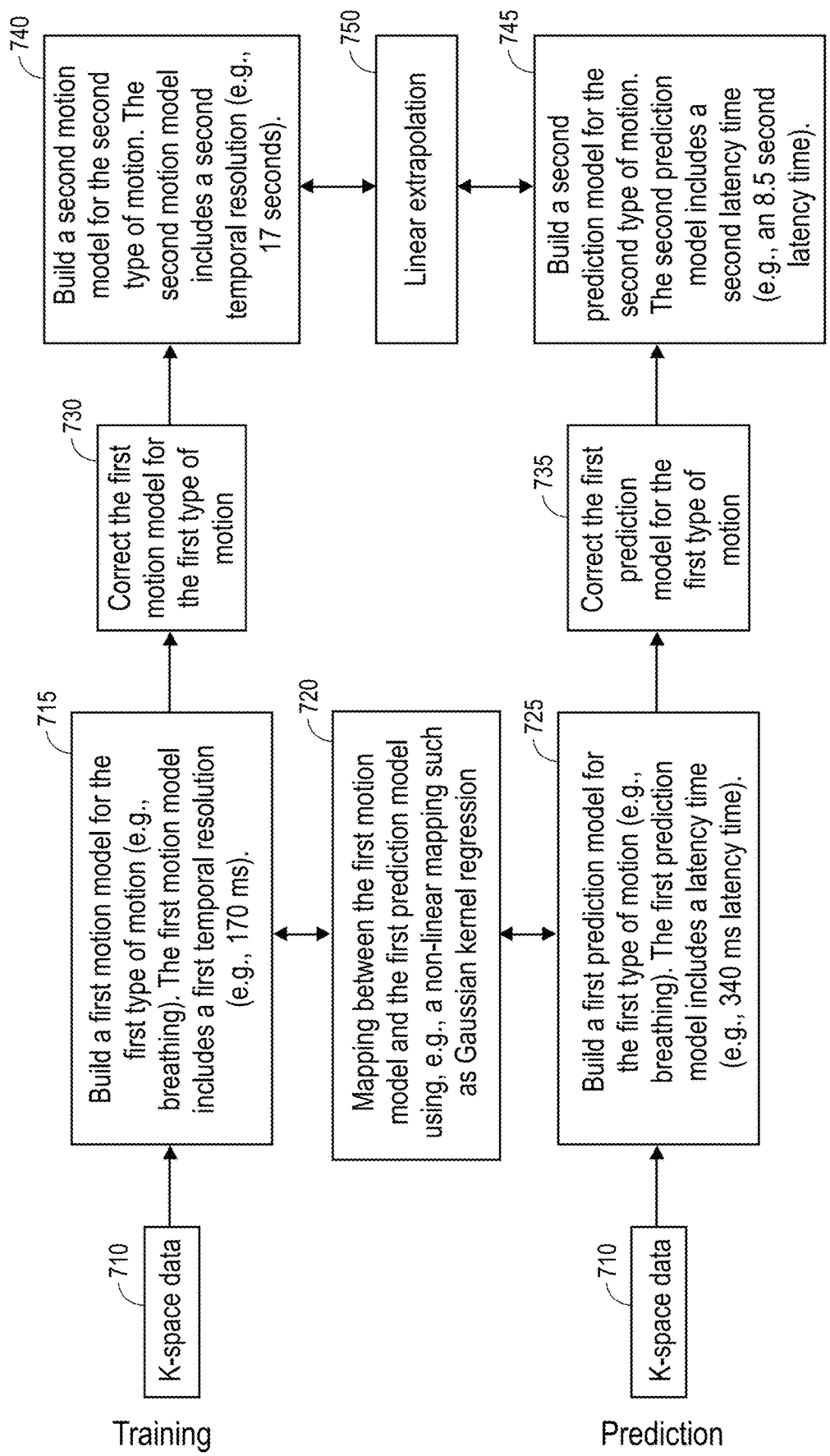
FIG. 7 shows an example flowchart of an embodiment using a multiple temporal technique.

Along these lines, FIG. 7 shows an example flowchart of an embodiment using a multiple temporal technique. With reference thereto, at step 715, the k-space data 710 is used to build a first motion model for a first type of motion (e.g., the breathing motion). In some embodiments, breathing motion is estimated with a temporal rate of 170 ms (e.g., the model has a first temporal resolution of 170 ms).

At step 720, Gaussian kernel regression is used to learn a non-linear mapping between a k-space sample and the associated motion model parameter, which in this exemplary case is the coefficient of the leading Principal Component projected to samples in the future. The appropriate deformation field is reconstructed using this estimated motion model parameter. The predicted motion state is estimated by deforming the reference state with the reconstructed deformation field.

Figure 8A:
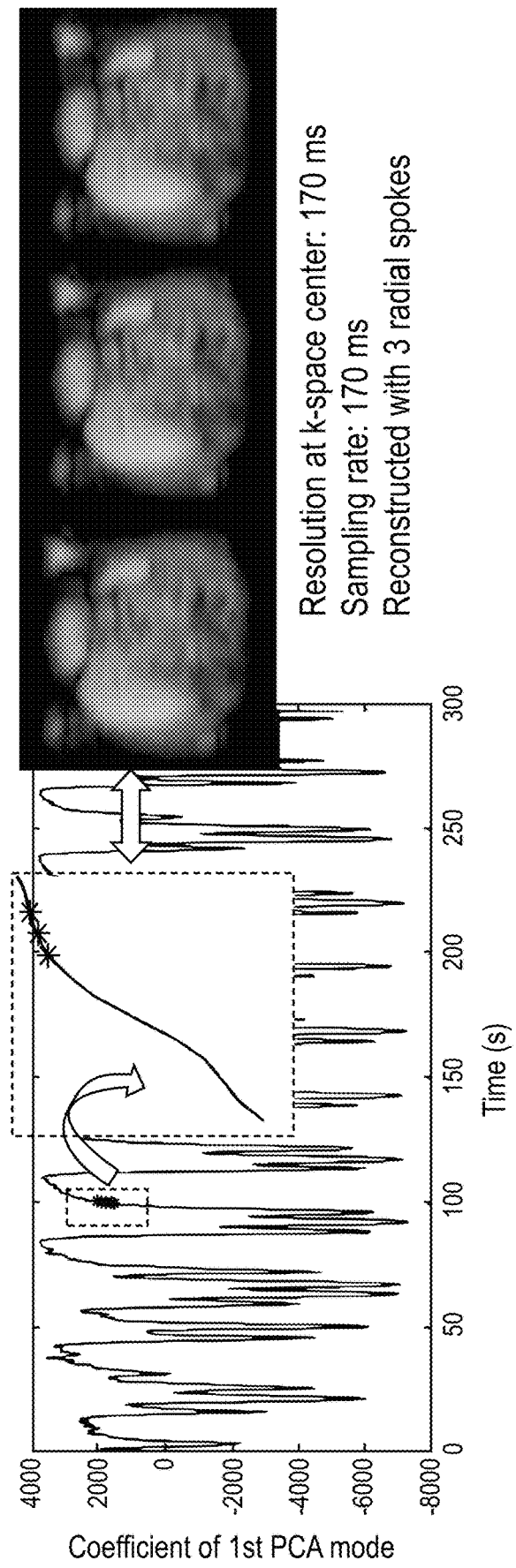
FIG. 8A shows an example implementation of a non-linear mapping between (i) high temporal and low spatial resolution image samples, and (ii) the principle component analysis (PCA) coefficient.
Figure 8B:
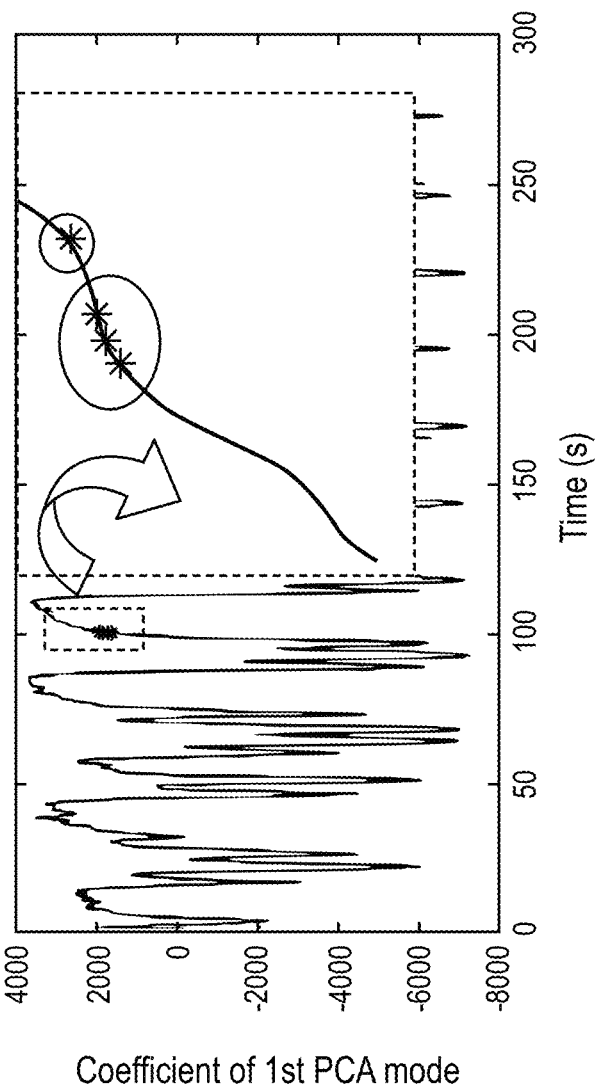
FIG. 8B illustrates a non-linear mapping between (i) three consecutive samples (170 ms sample rate), and (ii) a future state (340 ms ahead).

In this regard, FIGS. 8A and 8B show an example implementations of step 720, including an illustration of time vs the coefficient of first principle component analysis (PCA) mode. Specifically, FIG. 8A shows an example implementation of a non-linear mapping between (i) high temporal and low spatial resolution image samples, and (ii) the PCA coefficient. And, FIG. 8B illustrates a non-linear mapping between (i) three consecutive samples (170 ms sample rate), and (ii) a future state (340 ms ahead).

At step 725, a first prediction model is built for the first type of motion using the k-space data 710. System latency is accounted for by predicting motion associated with the k-space data 710 that is 340 ms ahead of the acquisition (e.g., the prediction model estimates the motion state 340 ms in the future, permitting this latency time for the treatment delivery system to react to the measurement).

Figure 9:
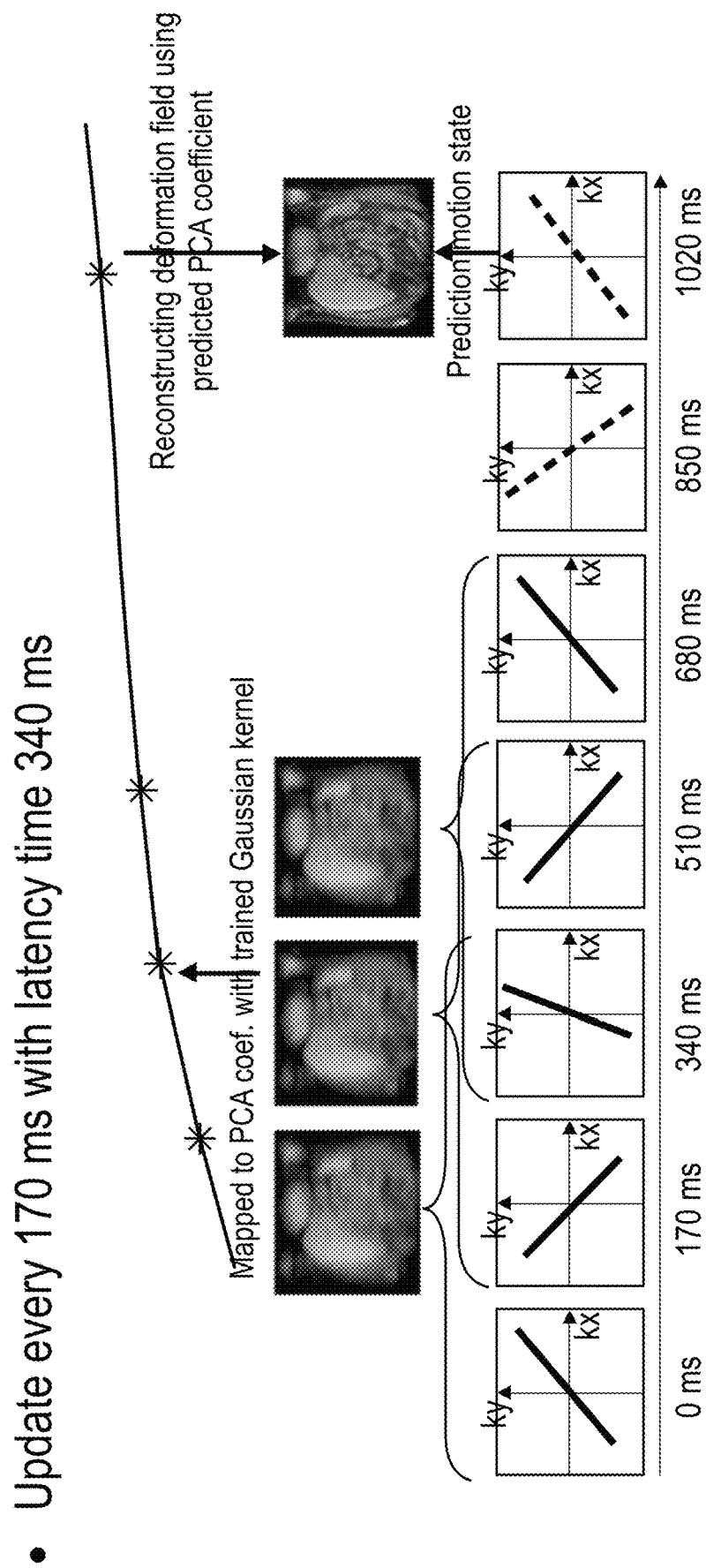
FIG. 9 shows an example implementation of building a prediction model.

In this regard, FIG. 9 shows an example implementation of step 725. Specifically, FIG. 9 shows an example implementation of building a prediction model supporting a latency time of 340 ms.

At step 730, correction is done to the first motion model for the first type of motion. At step 735, correction is done to the first prediction model to correct for the first type of motion.

Figure 10:
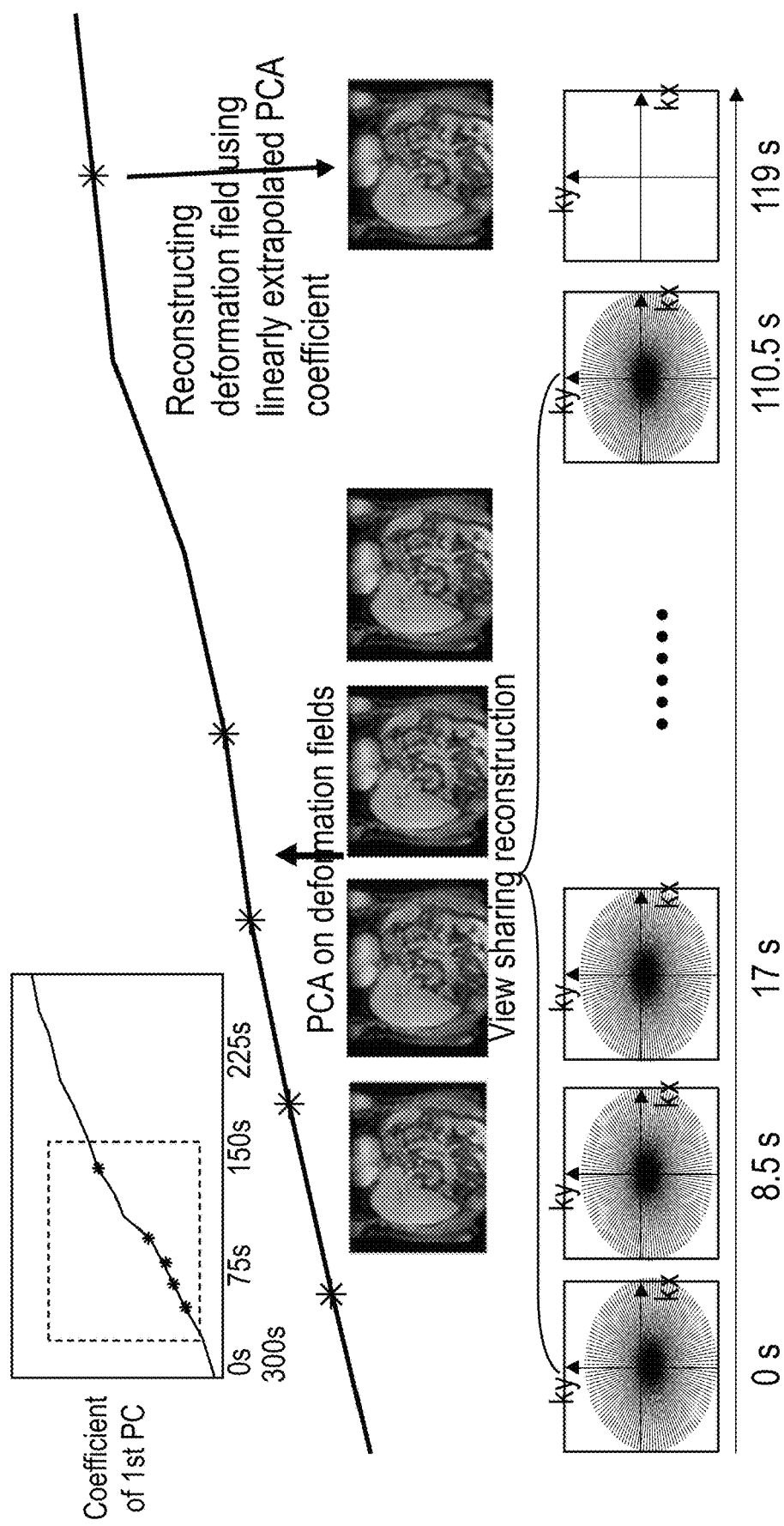
FIG. 10 shows an example implementation of building a second prediction model.

At step 740, a second motion model is built for a second type of motion (e.g., a gastric motion). And, at step 745, a second prediction model is built for the second type of motion. In this regard, in one example implementation, slow configuration changes are estimated on reconstructions of breathing motion-corrected projections with a slower temporal rate of 17 seconds and permitting a longer latency time of 8.5 seconds. In this regard, FIG. 10 shown an example implementation of step 745. For slow motions, the motion model is constructed by a sliding window Principal Component Analysis which includes the four most recent deformation fields. The Principal Component coefficient of a future motion state that is 8.5 seconds ahead of acquisition is estimated by linearly extrapolating (e.g., at step 750) observed coefficients and then used to reconstruct the associated deformation field. Preliminary experiments with this multitemporal resolution motion model indicate the ability to project the configuration of tumor and normal organ configurations with better than 1 mm accuracy for breathing and better than 0.5 mm accuracy for slow drifting motion for projected future states 0.34 seconds ahead of measurements for breathing and 8.5 seconds ahead of measurements for slower motions.

Other Matters

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of geographic locations.

What is claimed:

1. A computer-implemented method for real time display of a magnetic resonance (MR) image using a multitemporal technique, the method comprising, via one or more processors:

receiving k-space data acquired from an MR signal;

using the k-space data to:

(i) build a motion model, wherein the motion model includes a first temporal resolution; and (ii) build a prediction model, wherein the prediction model includes a first prediction latency time;

correcting both the motion model and the prediction model to account for a first type of patient motion;

displaying the MR image based on both the corrected motion model and the corrected prediction model; and correcting the motion model for a second type of patient motion using a second temporal resolution that is longer than the first temporal resolution, and wherein the MR image is displayed further based on the motion model corrected for the second type of patient motion.

2. The computer-implemented method of claim 1, wherein the first type of patient motion comprises a breathing motion, and the second type of patient motion comprises a gastric motion.

3. A computer-implemented method for real time display of a magnetic resonance (MR) image using a multitemporal technique, the method comprising, via one or more processors:
receiving k-space data acquired from an MR signal;
using the k-space data to:
(i) build a motion model, wherein the motion model includes a first temporal resolution; and
(ii) build a prediction model, wherein the prediction model includes a first prediction latency time;
correcting both the motion model and the prediction model to account for a first type of patient motion;
displaying the MR image based on both the corrected motion model and the corrected prediction model; and
correcting the prediction model for a second type of patient motion using a second latency time that is longer than the first prediction latency time, and wherein the MR image is displayed further based on the prediction model corrected for the second type of patient motion.

4. A computer-implemented method for real time display of a magnetic resonance (MR) image using a multitemporal technique, the method comprising, via one or more processors:
receiving k-space data acquired from an MR signal;
using the k-space data to:
(i) build a motion model, wherein the motion model includes a first temporal resolution; and
(ii) build a prediction model, wherein the prediction model includes a first prediction latency time;
correcting both the motion model and the prediction model to account for a first type of patient motion;
displaying the MR image based on both the corrected motion model and the corrected prediction model;
correcting the motion model for a second type of patient motion using a second temporal resolution that is longer than the first temporal resolution;
correcting the prediction model for a second type of patient motion using a second latency time that is longer than the first prediction latency time; and
linearly extrapolating between the motion model corrected for the second type of patient motion, and the prediction model corrected for the second type of patient motion, and wherein the MR image is displayed further based on the linear extrapolation.

5. A computer-implemented method for real time display of a magnetic resonance (MR) image using a multitemporal technique, the method comprising, via one or more processors:
receiving k-space data acquired from an MR signal;
using the k-space data to:
(i) build a motion model, wherein the motion model includes a first temporal resolution; and
(ii) build a prediction model, wherein the prediction model includes a first prediction latency time;
correcting both the motion model and the prediction model to account for a first type of patient motion;
displaying the MR image based on both the corrected motion model and the corrected prediction model; and
mapping between the motion model and the prediction motion model using Gaussian kernel regression.

6. A computer-implemented method for real time display of a magnetic resonance (MR) image using a multitemporal technique, the method comprising, via one or more processors:
receiving k-space data acquired from an MR signal;
using the k-space data to:
(i) build a motion model, wherein the motion model includes a first temporal resolution; and
(ii) build a prediction model, wherein the prediction model includes a first prediction latency time;
correcting both the motion model and the prediction model to account for a first type of patient motion; and
displaying the MR image based on both the corrected motion model and the corrected prediction model; and
wherein the k-space data includes a sampling rate, and the first temporal resolution is equal to the sampling rate.

7. The computer-implemented method of claim 6, wherein the sampling rate and the first temporal resolution are 170 ms.

8. The computer-implemented method of claim 1, wherein the first type of motion is a breathing motion, and wherein the correction of the motion model for the first type of motion occurs by:
determining a plurality of spokes in the k-space data;
labeling at least one spoke of the plurality of spokes with a breathing amplitude of a patient;
placing the at least one spoke into a bin of a plurality of bins, wherein each bin of the plurality of bins corresponds to a breathing state of a plurality of breathing states, and wherein one breathing state of the plurality of breathing states is an exhale state;
selecting the exhale state as a reference state; and
deformably aligning the other breathing states to the reference state.

9. A computer-implemented method for real time display of a magnetic resonance (MR) image, the method comprising, via one or more processors:
receiving k-space data acquired from an MR signal;
determining the MR image from the k-space data;
correcting the MR image to account for a first type of motion, wherein the first type of motion comprises a breathing motion, and wherein the correcting the MR image for the first type of motion occurs by:
(i) determining a plurality of spokes in the k-space data;
(ii) labeling at least one spoke of the plurality of spokes with a breathing amplitude of a patient;
(iii) placing the at least one spoke into a bin of a plurality of bins, wherein each bin of the plurality of bins corresponds to a breathing state of a plurality of breathing states, and wherein one breathing state of the plurality of breathing states is an exhale state;
(iv) selecting the exhale state as a reference state; and
(v) deformably aligning the other breathing states to the reference state; and
correcting, to account for a second type of motion, the MR image that was corrected for the first type of motion; and
wherein the second type of motion is a gastric motion.

10. A computer-implemented method for real time display of a magnetic resonance (MR) image, the method comprising, via one or more processors:
receiving k-space data acquired from an MR signal;
determining the MR image from the k-space data;
correcting the MR image to account for a first type of motion, wherein the first type of motion comprises a breathing motion, and wherein the correcting the MR image for the first type of motion occurs by:

(i) determining a plurality of spokes in the k-space data;
(ii) labeling at least one spoke of the plurality of spokes with a breathing amplitude of a patient;
(iii) placing the at least one spoke into a bin of a plurality of bins, wherein each bin of the plurality of bins corresponds to a breathing state of a plurality of breathing states, and wherein one breathing state of the plurality of breathing states is an exhale state;
(iv) selecting the exhale state as a reference state; and
(v) deformably aligning the other breathing states to the reference state; and correcting, to account for a second type of motion, the MR image that was corrected for the first type of motion; and the breathing motion has a first periodicity; and
the second type of motion has a second periodicity that is longer than the first periodicity.

11. A computer-implemented method for real time display of a magnetic resonance (MR) image, the method comprising, via one or more processors:
receiving k-space data acquired from an MR signal;
determining the MR image from the k-space data;
correcting the MR image to account for a first type of motion, wherein the first type of motion comprises a breathing motion, and wherein the correcting the MR image for the first type of motion occurs by:
(i) determining a plurality of spokes in the k-space data;
(ii) labeling at least one spoke of the plurality of spokes with a breathing amplitude of a patient;
(iii) placing the at least one spoke into a bin of a plurality of bins, wherein each bin of the plurality of bins corresponds to a breathing state of a plurality of breathing states, and wherein one breathing state of the plurality of breathing states is an exhale state;
(iv) selecting the exhale state as a reference state; and
(v) deformably aligning the other breathing states to the reference state; and correcting, to account for a second type of motion, the MR image that was corrected for the first type of motion; and wherein the correcting the MR image for the second type of motion comprises:
defining, in the MR image corrected for the first type of motion, a volume of interest (VOI) comprising a plurality of voxels;
extracting an unfiltered time-intensity curve for each voxel of the plurality of voxels;
temporally filtering the unfiltered time-intensity curves;
forming a power spectrum by summing power spectra of the temporally filtered time-intensity curves;
determining a mode frequency of the power spectrum;
creating new filtered curves by using the determined mode frequency to filter the unfiltered time-intensity curves;
extracting a single curve as a first principal component of the new filtered curves;
using the first principal component to determine a motion phase signal;
labeling at least one spoke of the plurality of spokes with a wave phase of the motion phase signal; and
binning the labeled at least one spoke based on a motion phase.

12. The computer-implemented method of claim 11, wherein the VOI encompasses a stomach of the patient.

13. A computer-implemented method for real time display of a magnetic resonance (MR) image, the method comprising, via one or more processors:
receiving k-space data acquired from an MR signal;
determining the MR image from the k-space data;
correcting the MR image to account for a first type of motion, wherein the first type of motion comprises a breathing motion, and wherein the correcting the MR image for the first type of motion occurs by:
(i) determining a plurality of spokes in the k-space data;
(ii) labeling at least one spoke of the plurality of spokes with a breathing amplitude of a patient;
(iii) placing the at least one spoke into a bin of a plurality of bins, wherein each bin of the plurality of bins corresponds to a breathing state of a plurality of breathing states, and wherein one breathing state of the plurality of breathing states is an exhale state;
(iv) selecting the exhale state as a reference state; and
(v) deformably aligning the other breathing states to the reference state; and correcting, to account for a second type of motion, the MR image that was corrected for the first type of motion; and wherein the correcting the MR image for the second type of motion comprises:
defining, in the MR image corrected for the first type of motion, a volume of interest (VOI) comprising a plurality of voxels;
creating a reference phase for the VOI;
determining, from the MR image corrected for the first type of motion, a set of image volumes demonstrating the second type of motion; and
deformably aligning the set of image volumes to the reference phase.

14. A computer-implemented method for real time display of a magnetic resonance (MR) image, the method comprising, via one or more processors:
receiving k-space data acquired from an MR signal;
determining the MR image from the k-space data;
correcting the MR image to account for a first type of motion; and
correcting, to account for a second type of motion, the MR image that was corrected for the first type of motion by:
defining, in the MR image corrected for the first type of motion, a volume of interest (VOI) comprising a plurality of voxels;
creating a reference phase for the VOI;
determining, from the MR image corrected for the first type of motion, a set of image volumes demonstrating the second type of motion; and
deformably aligning the set of image volumes to the reference phase.

15. The computer-implemented method of claim 14, wherein the deformably aligning the set of image volumes to the reference phase occurs by:
creating a binned state for each image volume of the set of image volumes;
determining a deformation field vector for each binned state; and
applying the deformation field vectors to spokes in the k-space data.

16. The computer-implemented method of claim 14, wherein the first type of motion is a breathing motion of a patient, and the second type of motion is a gastric motion of the patient.

17. The computer-implemented method of claim 14, wherein the second type of motion is a heartbeat motion of a patient.

18. The computer-implemented method of claim 14, wherein the second type of motion is a peristalsis motion of a patient.

19. The computer-implemented method of claim 14, further comprising:
   subsequent to the correction for the second type of motion, correcting for a third type of motion by:
   creating a volume reconstruction every n seconds, wherein n is a time period that is longer than a time period that the second type of motion occurs at.

\* \* \* \* \*

UNITED STATES PATENT AND TRADEMARK OFFICE
CERTIFICATE OF CORRECTION

PATENT NO. : 12,207,911 B2
APPLICATION NO. : 17/364845
DATED : January 28, 2025
INVENTOR(S) : James Balter et al.

Page 1 of 1

It is certified that error appears in the above-identified patent and that said Letters Patent is hereby corrected as shown below:

In the Claims

At Column 13, Line 14, below "and" insert -- wherein: -- as a new sub-point.

Signed and Sealed this
Second Day of September, 2025

Coke Morgan Stewart
*Acting Director of the United States Patent and Trademark Office*